United States Patent [19]

Dōya et al.

[11] Patent Number: 4,605,477
[45] Date of Patent: Aug. 12, 1986

[54] ELECTRODIALYTIC RECOVERY OF α-AMINO ACID FROM ITS AMIDE

[75] Inventors: Masaharu Dōya; Toshio Kondō; Hideo Igarashi; Takako Uchiyama, all of Niigata, Japan

[73] Assignee: Mitsubishi Gas Chemical Company, Inc., Japan

[21] Appl. No.: 704,596

[22] Filed: Feb. 25, 1985

[30] Foreign Application Priority Data

Mar. 1, 1984 [JP] Japan ................... 59-39496

[51] Int. Cl.$^4$ ............................................. B01D 13/02
[52] U.S. Cl. ................................................. 204/182.6
[58] Field of Search ...................................... 204/182.6

[56] References Cited

U.S. PATENT DOCUMENTS

| | | | |
|---|---|---|---|
| 1,986,920 | 1/1935 | Cross ............................ | 204/182.6 |
| 3,051,640 | 8/1962 | Traxler ......................... | 204/182.6 |
| 3,231,485 | 1/1966 | Kuwata et al. ................ | 204/182.6 |
| 3,330,749 | 7/1967 | Kuwata et al. ................ | 204/182.6 |
| 3,459,650 | 8/1969 | Hiraiwa et al. ............... | 204/182.6 |
| 4,238,306 | 12/1980 | Perry et al. .................. | 204/182.6 |
| 4,238,307 | 12/1980 | Perry et al. .................. | 204/182.6 |

Primary Examiner—John F. Niebling
Assistant Examiner—Terryence F. Chapman
Attorney, Agent, or Firm—Robbins & Laramie

[57] ABSTRACT

An α-amino acid is effectively separated and recovered from an aqueous solution containing at least an α-amino acid and its corresponding α-amino acid amide by performing ion-exchange electrodialysis in the presence of ammonia. A reaction product liquid obtained by biochemical asymmetric hydrolysis of a D, L-α-amino acid is used preferably as the raw material aqueous solution for dialysis.

13 Claims, 1 Drawing Figure on an industrial process for separating and recovering an L-α-amino acid from a solution containing an L-α-amino acid and a D-α-amino acid amide which is obtained by biochemical hydrolysis of a D, L-α-amino acid amide. As the result, it was found that it is possible to selectively separate and recover an L-α-amino acid alone by performing ion-exchange electrodialysis in the presence of ammonia. The present invention was completed based on this finding.

ELECTRODIALYTIC RECOVERY OF α-AMINO ACID FROM ITS AMIDE

BACKGROUND OF THE INVENTION

1. Field of the Invention

The present invention relates to a process for recovering an α-amino acid, and more particularly to a process for separating and recovering an α-amino acid from an aqueous solution containing an α-amino acid and its corresponding α-amino acid amide.

2. Description of the Prior Art

Upon biochemical asymmetric hydrolysis, a D, L-α-amino acid amide gives an L-α-amino acid and a D-α-amino acid amide. This process is known as one kind of optical resolution for D, L-α-amino acids. However, there have been no industrial process for separating and recovering an L-α-amino acid from the hydrolyzate.

The present inventors carried out extensive studies on an industrial process for separating and recovering an L-α-amino acid from a solution containing an L-α-amino acid and a D-α-amino acid amide which is obtained by biochemical hydrolysis of a D, L-α-amino acid amide. As the result, it was found that it is possible to selectively separate and recover an L-α-amino acid alone by performing ion-exchange electrodialysis in the presence of ammonia. The present invention was completed based on this finding.

SUMMARY OF THE INVENTION

Accordingly, it is an object of this invention to provide a process for separating and recovering an α-amino acid which comprising subjecting an aqueous solution containing at least an α-amino acid and its corresponding α-amino acid amide to ion-exchange electrodialysis in the presence of ammonia, said α-amino acid being represented by the general formula:

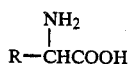

(where R denotes a hydrogen atom, lower alkyl group, substituted lower alkyl group, phenyl group, substituted phenyl group, furyl group, pyridyl group, thiazolyl group, imidazolyl group or indolyl group).

DETAILED DESCRIPTION OF THE INVENTION

Figure 1:
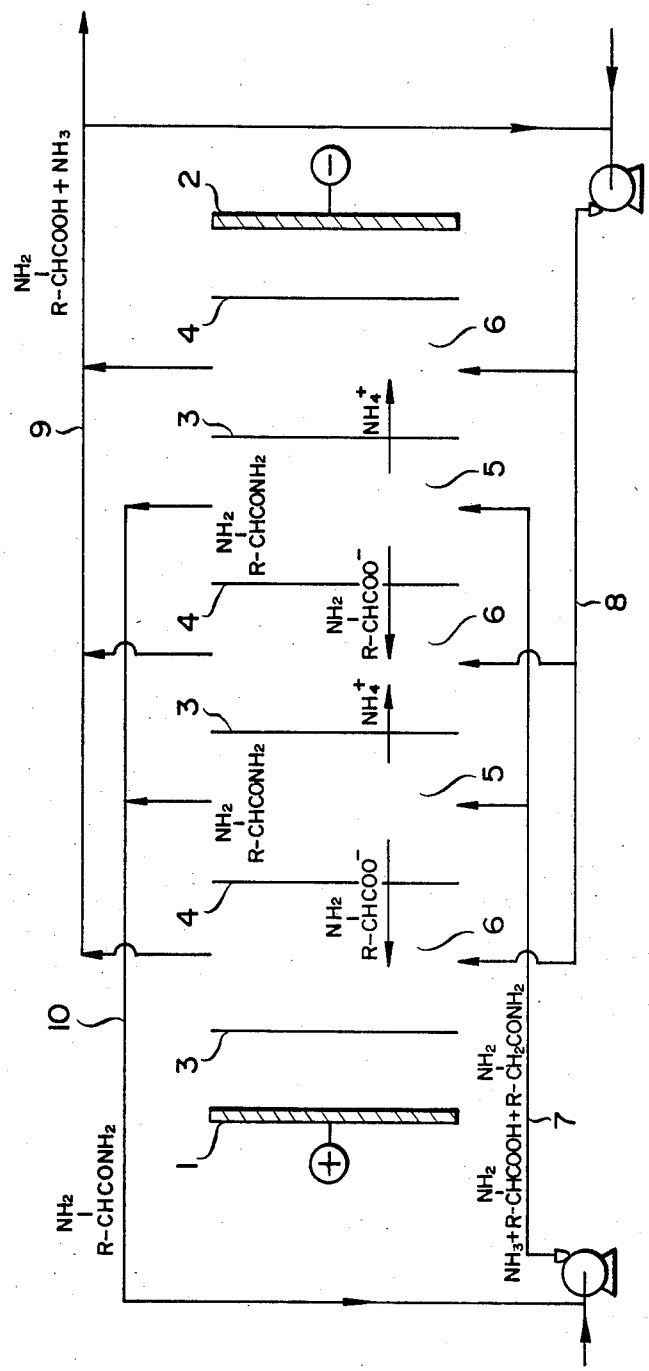
FIG. 1 is a schematic drawing of the ion-exchange electrodialyzer used in the process of this invention.

According to this invention, the lower alkyl group represented by R in the formula for an α-amino acid is not specifically limited. Preferred examples thereof include linear or branched lower alkyl groups having 1-4 carbon atoms such as methyl, ethyl, propyl, isopropyl, butyl, isobutyl, and sec-butyl. The substituent group in the substituted lower alkyl group or substituted phenyl group includes, for example, hydroxy, methyoxy, mercapto, methylmercapto, carboxamide, halogen, phenyl, hydroxyphenyl, indolyl or imidazolyl group.

Typical examples of the α-amino acid represented by the general formula above include glycine, alanine, valine, leucine, isoleucine, serine, threonine, cysteine, cystine, methionine, asparagine, glutamine, phenylglycine, phenylalanine, tyrosine, histidine or tryptophane.

The amount of ammonia in the raw material aqueous solution (hereinafter, referred to material solution) to be subjected to ion-exchange dialysis should be not less than equimolar with an α-amino acid in the material solution. There are no upper limits; but it should preferably be not more than 10 mol for 1 mol of α-amino acid. It is preferable from the economical point of view to use ammonia which is produced as a by-product during hydrolysis of an α-amino acid amide. Although ammonia and an α-amino acid are produced in equimolar amounts, it is desirable to add ammonia. If ammonia is less than an equimolar amount, the recovery of an α-amino acid will be low accordingly.

According to this invention, the ion-exchange dialysis can be performed by a conventional apparatus as well as under normal conditions. For example, the ion-exchange dialysis can be performed in the usual way with respect to applied voltage, electrode distance, number of ion-exchange membrane pairs, and space between ion-exchange membranes. Usually tens to hundreds of membrane pairs are used depending on the size of the apparatus.

The conditions under which the ion-exchange dialysis is performed may be different from the above condition. In this invention, the concentration of α-amino acid and α-amino acid amide in the material solution is respectively 0.1 to 20 wt %; the molar ratio of α-amino acid amide to α-amino acid is 0.01 to 100; and the temperature is 5° to 70° C., preferably 20° to 40° C. These conditions are not mandatory.

The material solution is an aqueous solution containing at least an α-amino acid represented by the general formula above and its corresponding α-amino acid amide. The material solution should preferably be a reaction product liquid containing at least an L-α-amino acid, D-α-amino acid amide and ammonia, which liquid is obtained by biochemical asymmetric hydrolysis of a D, L-α-amino acid amide. It is also possible to use a reaction product liquid containing an α-amino acid, a α-amino acid amide and ammonia, which liquid is obtained by hydrolyzing with heating an α-amino acid amide in the presence of ammonia.

The ion-exchange membrane used in this invention may be any ordinary one such as strongly acidic cation exchange membrane having sulfone groups and strongly basic anion exchange membrane having quaternary ammonium groups. Examples of the ion-exchange membranes are listed below.

"Selemion" CMV (strongly acidic cation exchange membrane)

"Selemion" AMV (strongly basic anion exchange membrane having quaternary ammonium groups)

(Both are products of Asahi Glass Co., Ltd.)

"Neosepter" CL-25T (strongly acidic cation exchange membrane)

"Neosepter" ACH-45T (strongly basic anion exchange membrane having quaternary ammonium groups)

(Both are products of Tokuyama Soda Co., Ltd.)

"Uplex" CK-1 (cation exchange membrane)

"Uplex" CA-2 (anion exchange membrane)

(Both are products of Asahi Chemical Industry Co., Ltd.)

The ion-exchange electrodialyzer used in the process of this invention is described with reference to FIG. 1, in which there are shown three each of cation-exchange membranes 3, 3, 3 and anion-exchange membranes 4, 4, 4 arranged alternately between an anode 1 and a cathode 2. Two membranes facing each other form a liquid feeding compartment 5 and a dialysis compartment 6 which are disposed alternately, provision is made so that solutions of different composition are passed through the respective compartments. Before and during dialysis, the dialysis compartments 6, 6, 6 are supplied with ammonia water or an aqueous solution containing an amino acid and ammonia through the feed pipe 8.

The material solution, which is an aqueous solution containing an α-amino acid, an α-amino acid amide and ammonia, is supplied to the liquid feeding compartments 5, 5 through the feed pipe 7. The α-amino acid and ammonia in the liquid feeding compartment 5 dissociate into monovalent anions and monovalent cations, the former migrating through the anion-exchange membranes 4 into the dialysis compartments 6 adjacent to the anode, and the latter migrating through the cation-exchange membranes 3 into the dialysis compartments 6 adjacent to the cathode, with the result that the amino acid amide remains in the liquid feeding compartments 5. As the material solution flows away from the entrance of the liquid feeding compartment 5, the concentrations of α-amino acid and ammonia decrease respectively and the concentration of α-amino acid amide increases. At the exit at opposite side of the entrance of the liquid feeding compartments 5, the concentration of α-amino acid and ammonia is extremely low respectively. The monovalent cations and monovalent anions which have migrated into the dialysis compartments 6, 6, 6 are collected in the aqueous solution (dialyzate) containing an α-amino acid and ammonia, and the dialyzate is discharged through the discharge pipe 9. The discharged dialyzate is concentrated by heating, evacuation, blowing, freezing and/or spraying to give a high-purity α-amino acid. A part of the dialyzate or ammonia water separated from the dialyzate may be recycled to the dialysis compartments 6, 6, 6 and this is preferable. The α-amino acid amide remaining in the liquid feeding compartments 5, 5 is discharged in the form of aqueous solution together with a very small amount of α-amino acid and ammonia, through the discharge pipe 10, and then is added to the material solution or recycled directly to the liquid feeding compartment 5, 5.

According to the process of this invention, it is possible to readily separate and recover an α-amino acid and an α-amino acid amide from the material solution and to obtain an α-amino acid of high purity.

The invention will be described in more detail with reference to the following examples, which should not be construed to restrict the scope of this invention.

EXAMPLE 1

Ion-exchange electrodialysis was carried out using an electrodialyzer, Model DU-06, (a product of Asahi Glass Co., Ltd.) equipped with 11 pairs of cation exchange membranes (Selemion CMV) and anion exchange membranes (Selemion AMV), each having an effective area of 209 cm². Two liters of material solution containing 1 mol of L-valine, 1 mol of D-valine amide and 1 mol of ammonia was supplied to the liquid feeding compartment of the dialyzer at room temperature. At the same time, 1.5 liters of 0.5 wt % ammonia water was supplied to the dialysis compartment. With the two solutions in the liquid feeding compartment and dialysis compartment circulating respectively and 10 V DC applied, dialysis was performed for 5 hours. The resulting dialyzate was analyzed by liquid chromatography. The content of L-valine was 0.97 mol and the content of D-valine amide was less than 0.01 mol (undetectable).

The dialyzate was concentrated under reduced pressure, followed by cooling for crystallization. The crystals were filtered out and dried. Thus there was obtained 107.8 g of 100% pure L-valine. The recovery of L-valine was 92.0 mol %.

EXAMPLE 2

Ion-exchange electrodialysis was carried out using the same dialyzer as in Example 1. Two liters of material solution containing 0.5 mol of L-methionine, 0.5 mol of D-methionine amide and 0.5 mol of ammonia was supplied to the liquid feeding compartment of the dialyzer at room temperature. At the same time, 1.5 liters of 0.5 wt % ammonia water was supplied to the dialysis compartment. With the two solutions in the liquid feeding compartment and the dialysis compartment circulating respectively and 10 V DC applied, dialysis was performed for 3 hours. The resulting dialyzate was analyzed by liquid chromatography. The content of L-methionine was 0.47 mol and D-methione amide was not detected.

EXAMPLE 3

Ion-exchange electrodialysis was carried out using the same dialyzer as in Example 1. Two liters of material solution containing 0.3 mol of L-phenylalanine, 0.3 mol of D-phenylalanine amide and 1 mol of ammonia was supplied to the liquid feeding compartment of the dialyzer at room temperature. At the same time, 1.5 liters of 0.5 wt % ammonia water was supplied to the dialysis compartment. With the two solutions in the liquid feeding compartment and the dialysis compartment circulating respectively and 10 V DC applied, dialysis was performed for 2 hours. The resulting dialyzate was analyzed by liquid chromatography. The content of L-phenylalanine was 0.28 mol and D-phenylalanine amide was not detected.

EXAMPLE 4

Ion-exchange electrodialysis was carried out using the same dialyzer as in Example 1. Two liters of material solution containing 2 mol of D-alanine, 0.1 mol of D-alanine amide and 2 mol of ammonia was supplied to the liquid feeding compartment of the dialyzer at room temperature. At the same time, 1.5 liters of 0.5 wt % ammonia water was supplied to the dialysis compartment. With the two solutions in the liquid feeding compartment and the dialysis compartment circulating respectively and 10 V DC applied, dialysis was performed for 7 hours. The resulting dialyzate was analyzed by liquid chromatography. The content of D-alaine was 1.95 mol and D-alanine amide was not detected.

EXAMPLE 5

Ion-exchange electrodialysis was carried out using the same dialyzer as in Example 1. Two liters of material solution containing 2 mol of glycine, 0.2 mol of glycine amide and 4 mol of ammonia was supplied to the liquid feeding compartment of the dialyzer at room temperature. At the same time, 1.5 liters of 0.5 wt % ammonia water was supplied to the dialysis compartment. With the two solutions in the liquid feeding compartment and the dialysis compartment circulating respectively and 10 V DC applied, dialysis was performed for 7 hours. The resulting dialyzate was analyzed by liquid chromatography. The content of glycine was 1.92 mol and glycine amide was not detected.

EXAMPLE 6

Ion-exchange electrodialysis was carried out using the same dialyzer as in Example 1. Two liters of material solution containing 0.3 mol of L-tryptophane, 0.3 mol of D-tryptophane amide, and 0.6 mol of ammonia was supplied to the liquid feeding compartment of the dialyzer at room temperature. At the same time, 1.5 liters of 0.5 wt % ammonia water was supplied to the dialysis compartment. With the two solutions in the liquid feeding compartment and the dialysis compartment circulating respectively and 10 V DC applied, dialysis was performed for 2 hours. The resulting dialyzate was analyzed by liquid chromatography. The content of L-tryptophane was 0.28 mol and D-tryptophane amide was not detected.

EXAMPLE 7

Ion-exchange electrodialysis was carried out using the same dialyzer as in Example 1. Two liters of material solution containing 0.2 mol of L-phenylglycine, 0.5 mol of D-phenylglycine amide and 0.2 mol of ammonia was supplied to the liquid feeding compartment of the dialyzer at room temperature. At the same time, 1.5 liters of 0.5 wt % ammonia water was supplied to the dialysis compartment. With the two solutions in the liquid feeding compartment and the dialysis compartment circulating respectively and 10 V DC applied, dialysis was performed for 2 hours. The resulting dialyzate was analyzed by liquid chromatography. The content of L-phenylglycine was 0.18 mol and D-phenylglycine amide was not detected.

EXAMPLE 8

(A) Into a reactor equipped with a stirrer were charged 2 liters of solution containing 2 mol of D, L-leucine amide in water (adjusted to pH 8.5 with HCl) and 200 mg of aminopeptidase (made by Sei-Kagaku Kogyo K.K.). Reaction with stirring was performed at 37° C. for 20 hours. The reaction product liquid was analyzed by liquid chromatography. The content of L-leucine was 0.98 mol, the content of L-leucine amide was 0.02 mol, the content of D-leucine amide was 1.00 mol and the content of ammonia by-produced was 0.98 mol.

(B) Electrodialysis was carried out using the same dialyzer as in Example 1. All the reaction product liquid obtained in step (A) was supplied to the liquid feeding compartment and, at the same time, 1.5 liters of 0.5 wt % ammonia water was supplied to the dialysis compartment. With the two solutions in the liquid feeding compartment and the dialysis compartment circulating respectively and 10 V DC applied, dialysis was performed for 6 hours. The resulting dialyzate was analyzed by liquid chromatography. The content of L-leucine was 0.96 mol and leucine amide was not detected.

The dialyzate was concentrated under reduced pressure, followed by cooling for crystallization. The crystals were filtered out and dried. Thus there was obtained 120.7 g (0.92 mol) of 100% pure L-leucine.

EXAMPLE 9

(A) Into a 2 liter reactor equipped with a stirrer were charged 2 mol of aminoacetamide and 1.5 liters of 10 wt % ammonia water. Reaction with stirring was performed at 150° C. for 5 hours. The reaction product liquid was analyzed by liquid chromatography. The content of glycine was 1.85 mol, the content of glycine amide was 0.07 mol and the content of ammonia was 10.67 mol.

(B) Electrodialysis was carried out using the same dialyzer as in Example 1. All the reaction product liquid obtained in step (A) was supplied to the liquid feeding compartment and, at the same time, 1.5 liters of 0.5 wt % ammonia water was supplied to the dialysis compartment. With the two solutions in the liquid feeding compartment and the dialysis compartment circulating respectively and 10 V DC applied, dialysis was performed for 8 hours. The resulting dialyzate was analyzed by liquid chromatography. The content of glycine was 1.81 mol and glycine amide was not detected.

The dialyzate was concentrated under reduced pressure, followed by cooling for crystallization. The crystals were filtered out and dried. Thus there was obtained 126.4 g (1.68 mol) of 100% pure glycine.

COMPARATIVE EXAMPLE 1

Example 1 was repeated except that the material solution containing no ammonia was used. According to the analysis by liquid chromatography, the content of L-valine was 0.05 mol and the content of D-valine amide was 0.01 mol in the dialyzate.

What is claimed is:

1. A process for separating and recovering an α-amino acid which comprises subjecting an aqueous solution containing at least an α-amino acid and its corresponding α-amino acid amide to ion-exchange electrodialysis in the presence of ammonia, wherein the mol ratio of ammonia to α-amino acid is not less than 1 in a raw material aqueous solution, said α-amino acid being represented by the general formula:

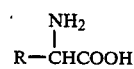

where R denotes a hydrogen atom, lower alkyl group, substituted lower alkyl group, phenyl group, substituted phenyl group, furyl group, pyridyl group, thiazolyl group, imidazolyl group or indolyl group.

2. A process for separating and recovering an α-amino acid as claimed in claim 1 wherein the lower alkyl group or the lower alkyl groups in the substituted lower alkyl group represented by R in the formula is a $C_1$–$C_4$ linear or branched lower alkyl group.

3. A process for separating and recovering an α-amino acid as claimed in claim 1 wherein the substituent group of the substituted lower alkyl group or substituted phenyl group represented by R in the formula is a hydroxy, methoxy, mercapto, methylmercapto, carboxamide, halogen, phenyl, hydroxyphenyl, indolyl or imidazolyl group.

4. A process for separating and recovering an α-amino acid as claimed in claim 1 wherein the α-amino acid is a glycine, alanine, valine, leucine, isoleucine, serine, threonine, cysteine, cystine, methionine, asparagine, glutamine, phenylglycine, phenylalanine, tyrosine, histidine or tryptophane.

5. A process for separating and recovering an α-amino acid as claimed in claim 1, wherein the molar ratio of ammonia to α-amino acid is within the range of 1 to 10 in the raw material aqueous solution.

6. A process for separating and recovering an α-amino acid as claimed in claim 1 wherein the ammonia in the raw material aqueous solution is a by-product produced by hydrolysis of an α-amino acid amide.

7. A process for separating and recovering an α-amino acid as claimed in claim 1 wherein each concentration of α-amino acid and α-amino acid amide in the raw material aqueous solution is 0.1 to 20 wt %.

8. A process for separating and recovering an α-amino acids as claimed in claim 1 wherein the molar ratio of α-amino acid to α-amino acid amide in the raw material aqueous solution is 0.01 to 100.

9. A process for separating and recovering an α-amino acid as claimed in claim 1 wherein the ion-exchange electrodialysis is performed with the liquid temperature at 5° to 70° C.

10. A process for separating and recovering an α-amino acid as claimed in claim 1 wherein the raw material aqueous solution is a reaction product liquid containing at least an L-α-amino acid, a D-α-amino acid amide and ammonia, which liquid is obtained by biochemical asymmetric hydrolysis of a D, L-α-amino acid.

11. A process for separating and recovering an α-amino acid as claimed in claim 1 wherein the raw material aqueous solution is a reaction product liquid containing at least an α-amino acid, an α-amino acid amide and ammonia, which liquid is obtained by hydrolyzing an α-amino acid amide in the presence of ammonia.

12. A process for separating and recovering an α-amino acid as claimed in claim 1 wherein the electrodialysis is performed using strongly acidic cation exchange membranes.

13. A process for separating and recovering an α-amino acid as claimed in claim 1 wherein the electrodialysis is performed using strongly basic anion exchange membranes.

* * * * *